United States Patent [19]
Hedberg

[11] Patent Number: 5,431,682
[45] Date of Patent: Jul. 11, 1995

[54] IMPLANTABLE HEART DEFIBRILLATOR

[75] Inventor: Sven-Erik Hedberg, Kungsaengen, Sweden

[73] Assignee: Pacesetter AB, Solna, Sweden

[21] Appl. No.: 114,922

[22] Filed: Sep. 2, 1993

[30] Foreign Application Priority Data

Sep. 16, 1992 [CH] Switzerland .................. 9202663-2

[51] Int. Cl.⁶ ............................................. A61N 1/36
[52] U.S. Cl. ............................................... 607/5
[58] Field of Search .................................. 607/4–8

[56] References Cited

U.S. PATENT DOCUMENTS

| | | |
|---|---|---|
| 4,407,288 | 10/1983 | Langer et al. . |
| 4,559,946 | 12/1985 | Mower . |
| 4,637,397 | 1/1987 | Jones et al. . |
| 4,693,253 | 9/1987 | Adams . |
| 4,800,883 | 1/1989 | Winstrom . |
| 4,821,723 | 4/1989 | Baker, Jr. et al. . |
| 4,850,357 | 7/1989 | Bach, Jr. . |
| 4,940,054 | 7/1990 | Grevis et al. . |
| 4,998,531 | 3/1991 | Bocchi et al. . |
| 5,107,834 | 4/1992 | Ideker et al. . |
| 5,111,813 | 5/1992 | Charbonnier et al. . |

FOREIGN PATENT DOCUMENTS 0253505  1/1988  European Pat. Off. .

OTHER PUBLICATIONS

"Implantable Cardioverters and Defibrillators Current Problems in Cardiology," Troup, Year Book Medical Publishers, Inc. vol. XIV, No. 12, Dec., 1989, pp. 699ff.

Primary Examiner—William E. Kamm
Assistant Examiner—Marianne Parker
Attorney, Agent, or Firm—Hill, Steadman & Simpson

[57] ABSTRACT

An implantable heart defibrillator is equipped with at least one intracardiac defibrillation electrode. A post-therapy apparatus is arranged to emit, after a defibrillation pulse, at least one stimulation pulse through the defibrillation electrode, the stimulation pulse having energy far higher than the energy in a normal heart stimulation pulse for cardiac pacing, but less energy than a normal defibrillation pulse.

12 Claims, 2 Drawing Sheets

IMPLANTABLE HEART DEFIBRILLATOR

BACKGROUND OF THE INVENTION

1. Field of the Invention

The present invention relates to an implantable heart defibrillator with at least one intracardiac defibrillation electrode.

2. Description of the Prior Art

An apparatus for detecting and treating heart arrhythmias with both pacemaker stimulation and defibrillation shocks is known through U.S. Pat. No. 4,940,054 and Paul J. Troup, "Implantable Cardioverters and Defibrillators, Current Problems in Cardiology", Year Book Medical Publishers, Inc., Chicago, volume XIV, no. 12, December 1989, p. 699 ff.

Heart cells are affected by the defibrillation shock for a time following a defibrillation pulse, making cells around the stimulation electrode difficult to excite with ordinary stimulation pulses from a pacemaker.

SUMMARY OF THE INVENTION

An object of the present invention is to solve the above problem and to produce an implantable heart defibrillator which enables effective stimulation of the heart immediately after a defibrillation pulse has been emitted.

The above object is achieved in an implantable heart defibrillator constructed in accordance with the principles of the present invention having at least one intracardiac defibrillation electrode, and including a post-therapy apparatus which emits at least one stimulation pulse, after a defibrillation pulse, through the defibrillation electrode, the stimulation pulse having energy which is far higher than the energy in a normal heart stimulation pulse of the type used for cardiac pacing. The energy of the stimulation pulse, however, is less than the energy of a normal defibrillation pulse.

As is known to those in the field of cardiology, energy levels typically employed for ventricular defibrillation are in the range of 20 to 50 Joules for internal application, and the energy level of a typical pacing pulse is on the order of 0.04 millijoules or less. The aforementioned "normal defibrillation pulse" and "normal heart stimulation pulse" can therefore be considered to exhibit these respective energy levels.

Thus, one or more heart stimulation pulses with greatly increased energy in relation to the energy in a conventional pacemaker pulse are emitted by the heart defibrillator according to the invention. A larger number of heart cells are accessed in this way. A defibrillation electrode can be employed as the stimulation electrode. The defibrillator case or another defibrillation electrode can serve as the indifferent electrode.

In further embodiments of the defibrillator of the invention, a post-therapy apparatus is arranged to emit a series of stimulation pulses with increased energy for a selectable period of time after a defibrillation pulse. The period which elapses between the emission of a defibrillation pulse and the emission of the first stimulation pulse and the rate of the stimulation pulses are also selectable.

The stimulation pulses with increased energy can be monophasic or biphasic.

According to other embodiments of the defibrillator of the invention, the post-therapy apparatus contains at least one capacitor which is charged to a lower voltage than the defibrillator capacitor for emission of the stimulation pulses with increased energy. Alternatively, in the defibrillator according to the invention, the defibrillation capacitor can be utilized for emitting the stimulation pulses with increased energy. In this case, a circuit is provided for sensing the voltage across the defibrillator capacitor following a defibrillation pulse and, when necessary, limiting the charging to a lower voltage than for heart defibrillation.

As is known to those skilled in the field of cardiology, a typical defibrillation pulse has a duration in the range of approximately 2 to 8 milliseconds, and this value can be used as an approximate range for the aforementioned "duration of the defibrillation pulses".

The post-therapy apparatus also contains devices for shortening the duration of the stimulation pulses with increased energy compared to the duration of the defibrillation pulses.

Since the defibrillator according to the invention can advantageously even contain a pacemaker unit, a microprocessor can control both the pacemaker and defibrillation functions in the defibrillator according to the invention, both the capacitor charging and the rate of stimulation then being controlled by the microprocessor. So in this instance, the post-stimulation pulses with increased energy for follow-up treatment are sent to the defibrillation unit instead of to the pacemaker unit. After stimulation with pulses with increased energy, normal pacemaker operation with stimulation through conventional pacemaker electrodes can resume.

If a limited number of stimulation pulses with increased energy is to be emitted, the pulses can, according to another embodiment of the defibrillator of the invention, be each supplied by the same capacitor if the pulse durations are shortened. If a long series of stimulation pulses with increased energy is desired, the charging circuit for charging the capacitor can also be enabled during the follow-up treatment. After emission of a defibrillation pulse, the defibrillator capacitor may still have enough energy stored therein to supply the requisite stimulation pulses with increased energy. A circuit is provided for such instances to sense whether the defibrillator capacitor has sufficient energy stored therein. Another capacitor can be charged to an appropriate level in another embodiment of the defibrillator of the invention, and a microprocessor determines, according to a program, the manner by which the different capacitors deliver the stimulation pulses with increased energy.

In yet another embodiment of the defibrillator of the invention, a current regulator is connected in series with the defibrillator capacitor for limiting the current output when stimulation pulses with increased energy are emitted. A device, such as a switch transistor whose output varies with the voltage measured across a series resistor, can be used as a current regulating component. The voltage across the defibrillator capacitor can then be set to a relatively high level, i.e. many times higher than the amplitude of the stimulation pulses with increased energy, so that the capacitor contains a large amount of energy, permitting the delivery of a plurality of stimulation pulses.

Thus, the microprocessor can monitor the voltage of the capacitors and connect the next capacitor when the voltage of the preceding capacitor drops excessively. The entire charging operation and capacitor selection process can be preprogrammed.

DESCRIPTION OF THE PREFERRED EMBODIMENTS

Figure 1:
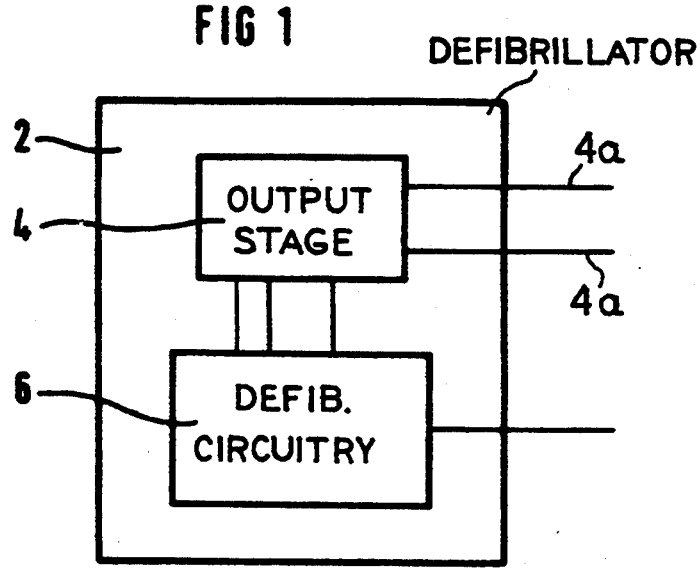
FIG. 1 shows a simplified block diagram of one embodiment of a defibrillator constructed according to principles of the invention.

In FIG. 1, one embodiment of a defibrillator according to the invention, which may be implantable, is shown in a simplified block diagram. The defibrillator 2 contains an output stage 4 and other defibrillation circuitry 6.

The output stage 4 contains the energy-storing capacitors, charging circuits, devices for measuring the current to the defibrillation electrodes and capacitor voltages, plus switches for controlling both defibrillation shocks and stimulation pulses with increased energy. Energy is supplied from the output stage 4 to a heart via one or more electrodes 4a, at least one of which is an intracardial electrode.

The circuitry 6 includes other parts of a defibrillator, such as a microprocessor for controlling the defibrillator 2. Thus, the microprocessor in the circuitry 6 determines which capacitor(s) in the output stage 4 are to be utilized for issuing stimulation pulses. When the energy in a capacitor becomes too low, the next capacitor is connected, etc. Since the course of post-therapy stimulation is known in advance, the microprocessor can be programmed to calculate which capacitors should be used. The starting point can be an estimated load between the defibrillation electrodes, or the resistance can be calculated from the impedance measured between the electrodes. Both the charging procedure and the choice of capacitors can be pre-programmed. The microprocessor in circuitry 6 monitors the voltage across the capacitors in the output stage 4 and connects the next capacitor when the preceding capacitor's voltage drops excessively. The times (intervals) for the pulse emission and the pulse widths are also controlled by the microprocessor in the circuitry 6.

Figure 2:
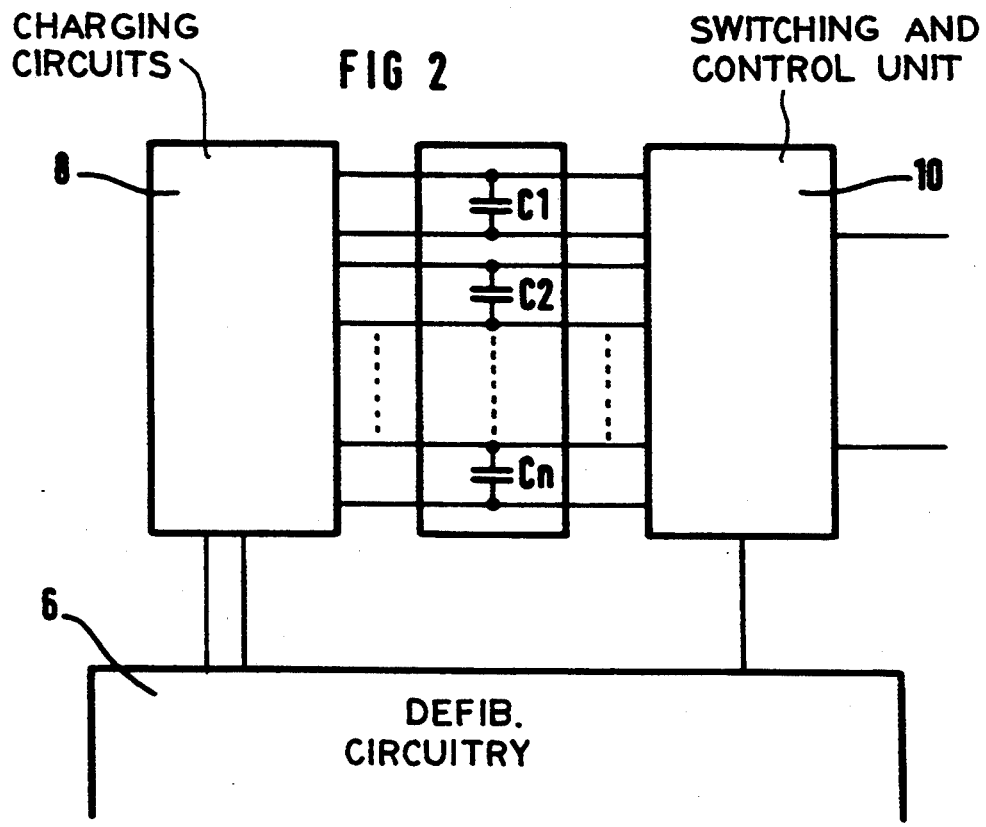
FIG. 2 shows a part of the defibrillator in FIG. 1 in a more detailed block diagram.

The output stage 4 contains charging circuits 8 for charging the capacitors $C_1, C_2, \ldots C_n$ to voltages determined by the defibrillator circuitry 6 (cf. FIG. 2). It is assumed that the capacitor $C_1$ in the output stage (cf. FIG. 2) constitutes the defibrillator capacitor and that other capacitors $C_2, \ldots C_n$ constitute auxiliary capacitors, especially arranged to issue stimulation pulses with increased energy.

The capacitors $C_1, C_2, \ldots C_n$ are discharged, via a switching and control unit 10, through the defibrillation electrodes 4a. Switches in the switching and control unit 10 are controlled by the circuitry 6, so the desired stimulation pulses with increased energy are obtained by discharge of the capacitors $C_1, C_2, \ldots C_n$ after the completion of defibrillation therapy.

Figure 3:
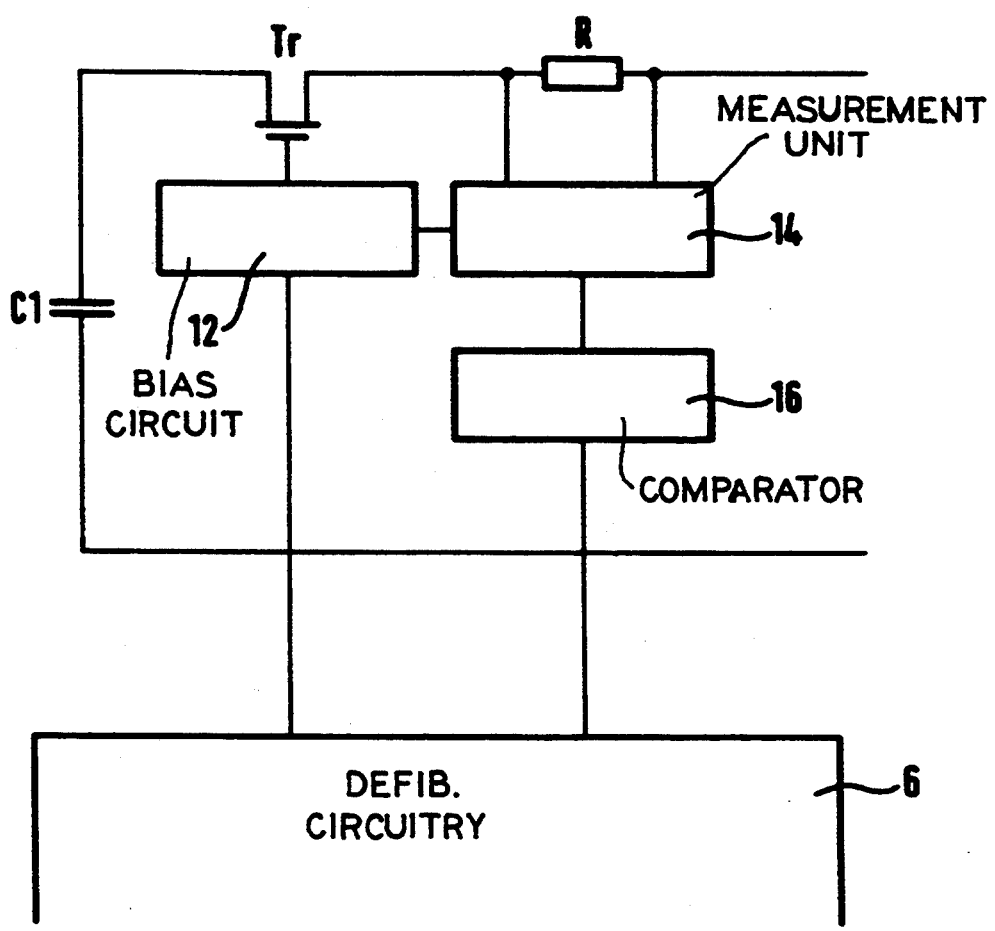
FIG. 3 is a block diagram showing the regulation of the output current from the capacitor in a defibrillator according to the invention when stimulation pulses with increased energy are emitted.

In FIG. 3, the control of the discharge of the capacitors is illustrated in greater detail.

The selection and the discharge of the capacitors preferably takes place according to a pre-programmed procedure.

Selection of capacitor $C_1, C_2, \ldots C_n$ is made via a time control signal supplied from the circuitry (such as from the microprocessor therein) to a bias circuit 12, which then opens the transistor Tr, causing a current to flow through the resistor R. The voltage across the resistor R is measured with the measurement unit 14 and compared in the comparator 16 to a reference value specified by the microprocessor in the circuitry 6. When the voltage reaches the reference value, the transistor Tr is cut off by the bias circuit 12 just enough to pass a current equal to the reference value. In this manner, output pulses are obtained with the desired intensity.

An additional transistor can also be connected to the capacitors, to avoid any internal connection between the other capacitors and the defibrillation electrodes, as is known from U.S. Pat. No. 4,800,883.

Although modifications and changes may be suggested by those skilled in the art, it is the intention of the inventors to embody within the patent warranted hereon all variations as reasonably and properly come within the scope of their contribution to the art.

I claim as my invention:

1. An implantable heart defibrillator comprising:

means for administering defibrillation therapy to the heart of a patient by delivering defibrillation pulses in vivo to said heart via at least one defibrillation electrode; and post-therapy means for delivering at least one stimulation pulse, after completion of said defibrillation therapy, to said heart via said defibrillation electrode, said stimulation pulse having energy significantly higher than a cardiac pacing pulse of approximately 0.04 millijoules and less than a defibrillation pulse of a range of 20–50 Joules.

2. A defibrillator as claimed in claim 1, wherein said post-therapy means comprising means for delivering a series of said stimulation pulses for a selectable period of time after a defibrillation pulse.

3. A defibrillator as claimed in claim 2, wherein said post-therapy means comprises means for emitting a first of said series of stimulation pulses at a selectable period of time after a defibrillation pulse.

4. A defibrillator as claimed in claim 2, wherein said post-therapy means comprises means for emitting said series of stimulation pulses at a selectable rate.

5. A defibrillator as claimed in claim 1, wherein said post-therapy means comprises at least one capacitor, and means for charging said capacitor to a first voltage for delivering defibrillation pulses and to a second voltage, lower than said first voltage, for delivery of said stimulation pulse.

6. A defibrillator as claimed in claim 5, wherein said post-therapy means includes means for sensing a voltage across said capacitor after delivery of a defibrillation pulse and for limiting charging of said capacitor to said second voltage for delivery of said stimulation pulse.

7. A defibrillator as claimed in claim 1, wherein said post-therapy means includes means for shortening a duration of said stimulation pulse in comparison to a duration range of said defibrillation pulse of 2 to 8 milliseconds.

8. A defibrillator as claimed in claim 1, wherein said post-therapy means includes a single capacitor, and means for successively charging and discharging said single capacitor for generating a series of said stimulation pulses.

9. A defibrillator as claimed in claim 1, wherein said means for administering defibrillation therapy contains a defibrillation capacitor, and wherein said post-therapy means includes means for charging and discharging said defibrillator capacitor for generating said stimulation pulse, and wherein said posttherapy means includes current regulator means connected in series with said defibrillator capacitor for limiting a current output from said defibrillator capacitor during the delivery of said stimulation pulse.

10. A defibrillator as claimed in claim 9, wherein said current regulator means contains a transistor connected in series with a resistor, means for measuring a voltage across said resistor and for controlling said transistor dependant on said voltage measured across said resistor.

11. A defibrillator as claimed in claim 10, wherein said means for measuring said voltage across said resistor includes means for comparing said voltage with a predetermined reference voltage, and for controlling said transistor to conduct a current corresponding to said reference voltage.

12. A defibrillator as claimed in claim 1, further comprising a plurality of capacitors and a microprocessor means for controlling charging and discharging of said capacitors for selectively generating and delivering said defibrillation pulse and said stimulation pulse according to a program.

* * * * *